(12) United States Patent
Peredultchuk et al.

(10) Patent No.: US 6,294,358 B1
(45) Date of Patent: Sep. 25, 2001

(54) THERMUS PROMOTERS FOR GENE EXPRESSION

(75) Inventors: Mikhail Peredultchuk; Veronica Vonstein, both of Chicago; David C. Demirjian, Hinsdale, all of IL (US)

(73) Assignee: Thermogen, Inc., Chicago, IL (US)

( * ) Notice: Subject to any disclaimer, the term of this patent is extended or adjusted under 35 U.S.C. 154(b) by 0 days.

(21) Appl. No.: 09/390,867

(22) Filed: Sep. 7, 1999

(51) Int. Cl.[7] .......................... C12P 21/00; C12N 15/00; C12N 15/74; C07H 21/04
(52) U.S. Cl. ..................... 435/69.1; 435/440; 435/477; 435/6; 435/320.1; 435/252.3; 536/23.1; 536/24.1
(58) Field of Search .................... 435/6, 440, 477, 435/69.1; 536/23.1, 24.1

(56) References Cited

U.S. PATENT DOCUMENTS

| | | | |
|---|---|---|---|
| 5,459,055 | 10/1995 | Jendrisak et al. | 435/199 |
| 5,786,174 | 7/1998 | Weber et al. | 435/69.1 |
| 5,872,238 | 2/1999 | Weber et al. | 536/23.7 |
| 5,969,121 | 10/1999 | Allen et al. | 536/23.1 |
| 5,981,177 | 11/1999 | Demirjian et al. | 435/6 |

FOREIGN PATENT DOCUMENTS 0138075    4/1985   (EP) .

OTHER PUBLICATIONS

Gryaznova, et al. Biochimie 78: 915–919, 1996.*

Lasa et al., "Insertional mutagenesis in the extreme thermophilic eubacteria *Thenus thermophilus* HB8," Molecular Microbiology, vol. 6, pp. 1555–1564, 1992.

Liao et al., "Isolation of a Thermostable enzyme variant by cloning and selection in a thermopile," Proc. Natl. Acad. Sci. USA, vol. 83, pp. 576–580, 1986.

Lerner et al., "Structure of the *Bacillus subtilus* pyrimidine biosynthetic (pyr) gene cluster," J. Bacterilogy, vol. 169, pp. 2202–2206, 1987.

Nagahari et al., "Cloning and expression of the leucine gene from the *Thermus thermophilus* in *Escherichia coli*," Gene, vol. 10, pp. 137–145, 1980.

Sen & Oriel, "Transfer to transposon Tn916 from*Bacillus subtilis* to *Thermus aquaticus*," FEMS Microbiology Letters 67:131–134 (1990).

Koyama et al., "A plasmid vector for an extreme thermophile, *Thermus thermophilus*," FEMS Microbiology Letters 72:97–102 (1990).

Koyama & Furukawa, "Cloning and Sequence Analysis f Tryptophan Synthease Genes of an Extreme Thermophile, *Thermus thermophilus* HB27: Plasmid transfer from Replica–Plated *Escherichia coli* Recombinant Colonies to Competent *T. Thermophilus* Cells," J. of Bacteriology, 172:3490–3495 (1990).

Koyama et al., "Genetic Transformation of the Extreme Thermophile *Thermus thermophilus* and of Other Thermus spp.," J. Bacteriology, 166:338–340 (1986).

Borges and Bergquist, "Genomic Restriction map of the Extrememly Thermophilic Bacterium *Thermus Thermophilus* HB8," J. Bacteriology, 175:103–110 (1993).

Matsumura et al., "Enzymatic and ucleotide Sequence Studies of a Kanamycin–Inactivating Enzyme Encoded by a Plasmid from *Thermophilic Bacilli* in Comparison with That encoded by Plasmid pUB110," J. of Bacteriology, 160:413–420 (1984).

Matsumura & Aiba, "Screening of Thermostable Mutant of Kanamycin Nucleotidyltransferase by the Use of a Transformation System for a Thermophile, *Bacillus stearothermophilus*," J. of Biological Chemistry, 260:15289–15303 (1985).

Matsumura et al., "Cumulative effect of intragenic amino–acid replacements on the thermostability of protein," Nature, 323:356–358 (1986).

Lasa et al., "Development of Thermus–Escherichia Shutle Vectores and Their Use of Expression of the *Clostridium thermocellum* CelA Gene in *Thermus thermophilus*," J. of Bacteriology, 174:6424–6431.

Faraldo et al., "Sequence of the S–Layer Gene of *Thermus thermophilus* HB7 and Functionality of its Promoter in *Escheria coli*," J. of Bacteriology, 174:7458–7462 (1992).

Mather & Fee, "Development of Plasmid Cloning Vectors for *Thermus thermophilus* HB8: Expression of a Heterologous, Plasmid–Bone Kanamycin Nucleotidyltransferase Gene," Applied and Enviro. Microbiology, 58:421–425 (1992).

(List continued on next page.)

Primary Examiner—David Guzo
Assistant Examiner—Gerald G. Leffers, Jr.

(57) ABSTRACT

The present invention relates to a system for identifying, isolating and utilizing promoter elements useful for expression of nucleotide sequences and the proteins encoded thereby in a thermophile. In one embodiment, a recombinant DNA molecule is provided, and comprises a reporter sequence, a putative thermophile promoter, a selectable marker sequence, and a 3' and a 5' DNA targeting sequence that are together capable of causing integration of at least a portion of said DNA molecule into the genome of a thermophile. Further, within the recombinant DNA, the reporter sequence is under the transcriptional control of a promoter which functions in a thermophile to form a promoter/reporter cassette, the promote/reporter cassette is flanked by said 3' and said 5' DNA targeting sequences, and the promoter/reporter cassette is positioned in the opposite orientation of the DNA targeting sequences.

9 Claims, 4 Drawing Sheets

OTHER PUBLICATIONS

Tanaka et al., "Cloning of 3–Isopropylmalate Dehydrogenase Gene of an Extreme Thermophile and Partial Purification of the Gene Product," Biochem., 89:677–682 (1981).

Croft et al., "Expression of the leucine genes from an extremely thermophilic bacterium in *Escheria coli*," Molec. Gen. Genet. 210:490–497 (1987).

Yamada et al., "Purfication, Catalytic Properties, and Thermal Stability of Thero –Ds–3–Isopropylmalate dehydrogenase Coded by euB Gene from an Extreme Thermophile *Thermus thermophilus* Strain HB8," J. Biochem., 105:449–456 (1990).

Kirino & Oshima, "Molecular Cloning and Nucleotide Sequence of 3–Isopropylmalate Dehydrogenase Gene (IeuB) from an Extreme Thermophile, *Thermus aquaticus* YT–1," J. Biochem., 109:852–857 (1991).

Imada et al., "Three–dimensional Structure of a Highly Thermostable Enzyme, 3–Isopropylmalate Dehydrogenase of *Thermus thermophilus* at 2.2 Å Resolution," J. Mol. Biol., 222:725–738 (1991).

Onodera et al., "Crystallization and Preliminary X–Ray Studies of a *Bacillus subtilis* and *Thrumus thermophilus* HB8 Chimeric 3–Isopropylmalate Dehydrogenase," J. Biochem., 109:1–2 (1991).

Lacey, R.W. and I. Chopra, "Genetic studies of multiresistant strain of *Staphylococcus aureus*," J. Med. Microbiol., 7:285–297 (1974).

Casadaban et al., "Beta–galactosidase gene fusions for analyzing gene expression in *Escherichia coli* and Yeast," Meth. in Enzymol., vol. 100, 293–308 (1983).

Maseda, et al, FEMS Microbiology Letters, vol. 128, pp. 127–134.

\* cited by examiner

Comparison of Terminators from *Thermus*.

```
<leu Termin.    TCCCCAGGA ACCTT:TTGC CGGGGCCCCC ATGCTGGGCG AAGCCAGCAT GGGGTGGTGT TACAGGTGCC GCAGA
<his terminator            CAGGG ACCTT:TTGC CGGGGCCCCC ATGCTGGGCG AAGCCAGCAT GGGGTGGCAT CAAAGCACCC C
<icd terminator                   CCATGC C:GGG:CCCC ATGCCGGCCC AAGCCGGCAT GGGGTGGCCT TA
<proC Terminator                  CCTTC:TGC CGGGGCCCCC ATGCGGGCGC AAGCC:G:AT GGGGTGGCCT CA
<phe S/T Terminator      GG GCCTT:TTGC CGGGGCCCCC ATGCTGGGCG AAGCCAGCAT GGGGTGGCAT TA
<pol Termin.    TTCCCCAGAA ACCTT:TTGC CGGGGCCCCC ATGCTGGCTT GGGCCAGCAT GGGGTGGTAT CA
```

FIG. 3A

THERMUS PROMOTERS FOR GENE EXPRESSION

FIELD OF THE INVENTION

The present invention relates to the identification and utilization of promoters for expression of nucleic acid sequences in thermophiles.

BACKGROUND OF THE INVENTION

The high-temperature operating conditions of certain industrial processes in the areas of pharmaceutical synthesis, biodegradation of complex agricultural and industrial waste compounds, and food processing dictate the use of thermostable enzymes that can function at high temperatures. A significant advantage thermostable enzymes provide are cost savings resulting from longer storage stability and the higher activity at high temperature.

Thermostable enzymes have traditionally been used for saccharification in food processing and proteolysis in detergent industry (Williams, R. A. D. Biotechnological applications of the genus Thermus. Thermophiles: Science and Technology, Reykjavik, Iceland, 1992). Glucosidases are utilized extensively throughout the starch processing industry. Thermostable carbohydrases are directly involved in the manufacture of all starch-derived products. Isomersases are involved in production of high-fructose corn syrup. Two other important industrial carbohydrases are the pectolytic enzymes and lactase (Burgess, K. and M. Shaw. In *Industrial enzymology*. Ed. by T. Godfrey and Reichelt, J., N.Y. p. p. 260. 1983; Bombouts, F. M. and W. Pilnik. In *Microbial enzymes and bioconversions*. Ed. by A. H. Rose, N.Y. p. 269. 1980). A recent development in the industrial enzyme area is the use of cellulase for the production of glucose from cellulose (Mandels, M. In *Annual reports on fermentation processes*. Ed. by G. T. Tsao, N.Y. p. 35. 1982). Proteolytic enzymes, constituting a significant segment of the total industrial enzyme market are utilized in the detergent industry (Godfrey, T. and J. Reichelt. (1983) Industrial enzymology.).

One of the most promising new applications of thermostable enzymes is in the manufacture of specialty chemicals and pharmaceutical intermediates. Enzymes (or biocatalysts) are now being viewed as clearly superior in cases where stereospecific synthetic reactions are involved, such as synthesis of chiral compounds as pharmaceutical intermediates. Enzymes can carry out the reaction more specifically and under conditions which are safer for the environment. Thermostable enzymes have advantages since they are generally more stable in organic solvents, can carry out reactions at high temperatures where substrate and product solubility is higher, and can be recycled and used for longer periods of time because of their inherent stability.

A relatively new application of thermostable enzymes is PCR-based diagnostics. Thermostable polymerases have been extremely useful in the detection and molecular characterization of agents causing cancer, AIDS, and numerous other infectious diseases. Thermostable DNA-polymerase can already compete in market value with enzymes having traditional applications. Thermostable DNA replication proteins have important applications in molecular biology research.

A significant limitation to the widespread use of thermostable enzymes in such applications is the difficulty in expressing the proteins in a host bacteria. Thermophilic bacteria belong to a wide range of very different taxonomic groups (Kristiansson, J. K. and K. O. Stetter. Thermophilic bacteria. In *Thermophilic bacteria*. Ed. by J. K. Kristiansson, CRC Press, Inc., Boca Raton. p. 1–18. 1992). One of the best studied is the gram negative genus Thermus. Species belonging to this genus are easy to handle, growing aerobically in a broad temperature range of 45 to 85° C. and not requiring pressurized incubation devices (Williams, R. A. D. Biotechnological applications of the genus Thermus. Thermophiles: Science and Technology, Reykjavik, Iceland, 1992). These strains grow to high densities in simple and inexpensive liquid media and form colonies on solid agar. With a doubling time less than 2 hours, the microorganisms of the genus Thermus are suitable organisms for various industrial applications.

Despite the widespread interest in Thermus cultures for a variety of applications, there is a need for systems to control gene expression in Thermus. Currently the expression of heterologous genes in thermophilic hosts is difficult and inconvenient. Expression vectors for thermophiles do not provide a choice of promoters or ribosome binding sites, nor do they provide a convenient ways to regulate expression. The reagents and methodologies provided herein allow for the production of commercially important enzymes including those from hyper- and extreme-thermophiles that can be difficult to produce using other systems. Also provided are reagents and methodologies for the construction of high-temperature fermentation strains which have been metabolically engineered with exogenous DNA for use in bioprocess applications such as production of complex molecules and pharmaceutical intermediates. Additionally, the systems provided herein are useful for thermostabilization of mesophilic proteins by genetic selection in a thermophile, which can also lead to altered enzymatic activity and a better understanding of the biochemical determinants for thermostability.

SUMMARY OF THE INVENTION

Figure 1:
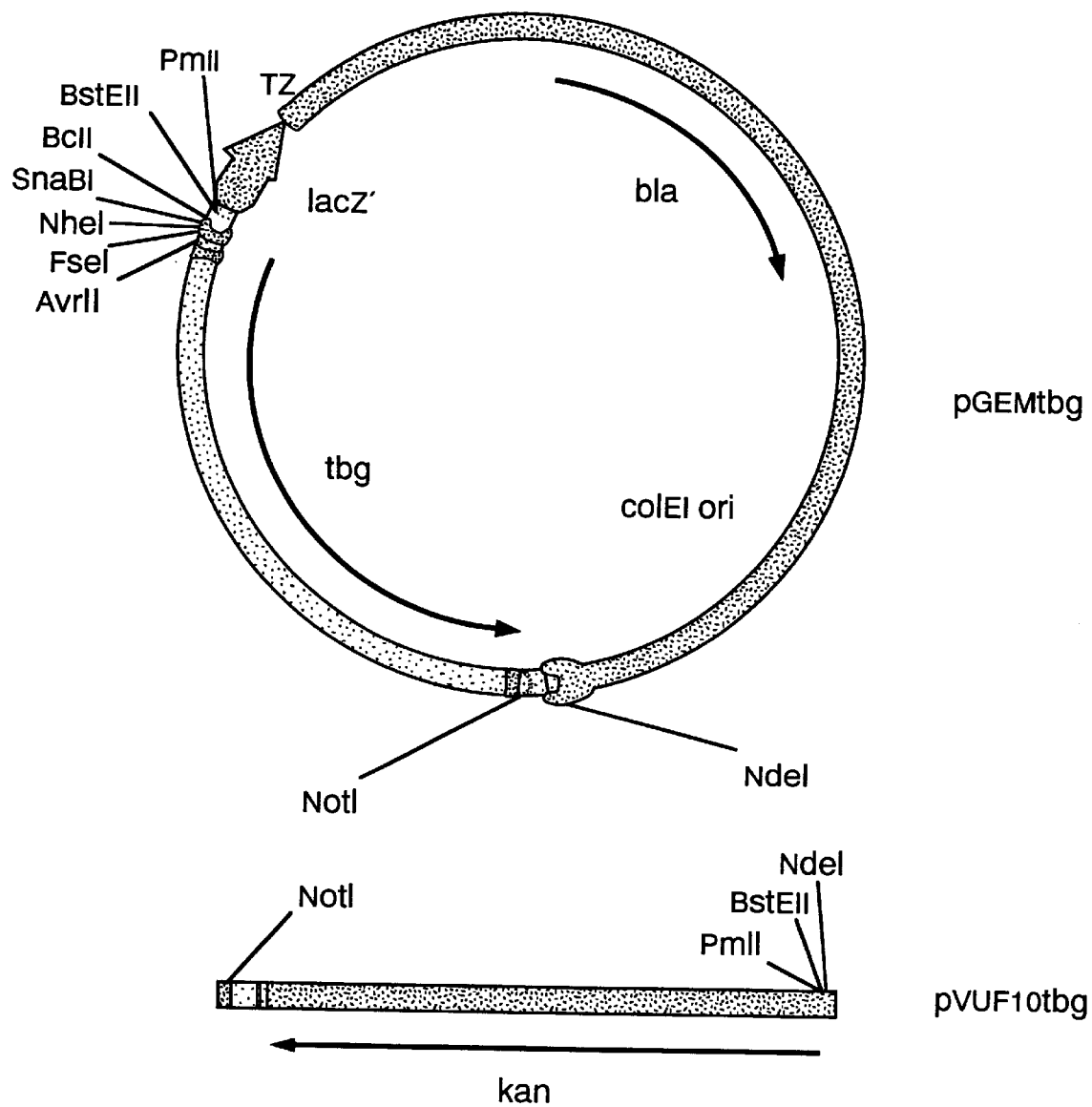
FIG. 1. Construction of an integrative promoter probe vector to look for Thermus promoters in *E. coli*
Figure 2:
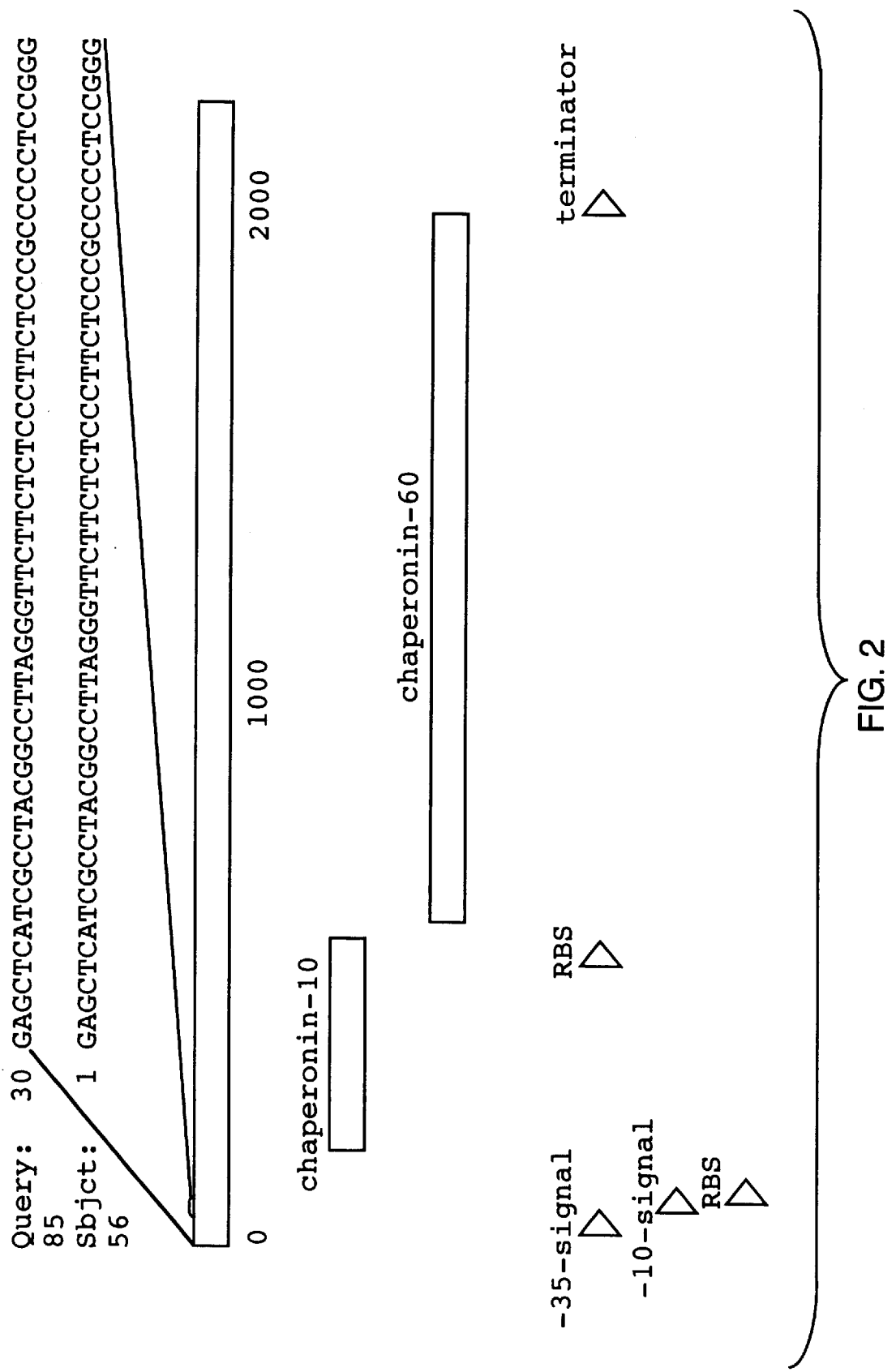
FIG. 2. Homology comparison of VV57 with the *T. thermophilus* chaperonin-10 and chaperonin-60 promoter region. The sequence derived from the VV57 promoter clone insert SEQ ID NO: 45 was subjected to BLASTN analysis and the resulting homology comparisons were analyzed. The VV57 sequence matched the promoter region containing the −35, −10 promoter signal sequences as well as the ribosomal binding site SEQ ID NO: 46.

The present invention relates to a system for identifying, isolating and utilizing promoter elements useful for expression of nucleotide sequences and the proteins encoded thereby in a thermophile. In one embodiment, a recombinant DNA molecule is provided, and comprises a reporter sequence, a putative thermophile promoter, a selectable marker sequence, and a 3' and a 5' DNA targeting sequence that are together capable of causing integration of at least a portion of said DNA molecule into the genome of a thermophile. Further, within the recombinant DNA, the reporter sequence is under the transcriptional control of a promoter which functions in a thermophile to form a promoter/reporter cassette, the promoter/reporter cassette is flanked by said 3' and said 5' DNA targeting sequences, and the promoter/reporter cassette is positioned in the opposite orientation of the DNA targeting sequences. In another embodiment, a method of identifying a thermophile promoter comprising transforming a thermophile with the above-described recombinant DNA molecule detecting expression of the reporter sequence is provided. The present invention also relates to promoters which have been identified by the above method.

DETAILED DESCRIPTION

Within this application, unless otherwise stated, definitions of the terms and illustration of the techniques of this application may be found in any of several well-known references such as: Sambrook, J., et al., *Molecular Cloning: A Laboratory Manual,* Cold Spring Harbor Laboratory Press (1989); Goeddel, D., ed., *Gene Expression Technology, Methods in Enzymology,* 185, Academic Press, San Diego, Calif. (1991); "Guide to Protein Purification" in Deutshcer, M. P., ed., Methods in *Enzymology,* Academic Press, San Diego, Calif. (1989); and, Innis, et al., *PCR Protocols: A Guide to Methods and Applications,* Academic Press, San Diego, Calif. (1990). The references, issued patents and pending patent applications cited herein are incorporated by reference into this application.

For the purposes of this application, a promoter is a regulatory sequence of DNA that is involved in the binding of RNA polymerase to initiate transcription of a gene. A "thermophile promoter" is a promoter that functions in a thermophilic organism such as Thermus. A gene is a segment of DNA involved in producing a peptide, polypeptide or protein, including the coding region, non-coding regions preceding ("leader") and following ("trailer") the coding region, as well as intervening non-coding sequences ("introns") between individual coding segments ("exons"). Coding refers to the representation of amino acids, start and stop signals in a three base "triplet" code. Promoters are often upstream ("'5 to") the transcription initiation site of the corresponding gene. Other regulatory sequences of DNA in addition to promoters are known, including sequences involved with the binding of transcription factors, including response elements that are the DNA sequences bound by inducible factors. Enhancers comprise yet another group of regulatory sequences of DNA that can increase the utilization of promoters, and can function in either orientation (5'-3' or 3'-5') and in any location (upstream or downstream) relative to the promoter. Preferably, the regulatory sequence has a positive activity, i.e., binding of an endogeneous ligand (e.g. a transcription factor) to the regulatory sequence increases transcription, thereby resulting in increased expression of the corresponding target gene. A promoter may also include or be adjacent to a regulatory sequence known in the art as a silencer. A silencer sequence generally has a negative regulatory effect on expression of the gene.

Provided herein are methodologies and reagents for obtaining and utilizing expression systems for efficient expression of nucleotide sequences in a host organism. Preferably, the host cell is a member of the kingdom Bacteria, Archea or Eukarya. In one embodiment, and for the purpose of testing the constructs provided herein, it is preferred that the host cell is *E. coli*. More preferably, it is preferred that the expression systems comprise promoter elements capable of regulating gene expression in a thermophile. Even more preferably, the host cell is a member of the genus Thermus, and most preferably the host cell is of the species *Thermus flavus, Thermus thermophilus, Thermus aquaticus* or other related species. The instant invention provides reagents and methodologies useful for identifying promoters having activity in a thermophile, preferably of the genus Thermus.

Using the reagents and techniques described in this application, inducible and constitutive promoters, integrative and plasmid-based vectors, and nucleic acids containing secretion signals may be isolated. The vectors utilized may be any vector suitable to isolation and characterization of a promoter. For instance, the vectors utilized may be plasmid, bacteriophage, virus, phagemid, cointegrate of one or more species, etc. Preferably, the vector is amenable to expression of a nucleotide sequence in a prokaryotic cell such as Thermus or *E. coli*. It is further preferable that the vectors be capable of functioning in different types of cells (ie, shuttle), such as Thermus or *E. coli*.

It is also possible to use the present invention to accomplish model pathway engineering and/or thermostabilization using tandem expression systems. The present invention provides promoter sequences and expression vectors that allow for various levels of expression in a thermophilic host cell. The levels of expression may be controlled by the inherent properties of the promoter itself or with the assistance of an additional regulatory sequence. The availability of such promoter sequences will provide a crucial tool for use in driving expression of thermostable enzymes for use in multiple applications.

As would be understood by the skilled artisan, the development of efficient thermophile expression systems is important for several applications including, for example, the isolation and use of nucleic acid sequences from extreme- or hyper-thermophiles that may not be efficiently expressed in mesophilic systems. Thousands of genes and uncharacterized ORFs have been discovered from these industrially important organisms through genome sequencing projects. High-temperature fermentation strains with altered metabolism may be useful in bioprocess applications for the production of pharmaceutical intermediates. The present invention provides tools for thermostabilizing mesophilic proteins by selection in Thermus and allows for the identification of the sequence determinants involved in thermostabilization.

In addition, the reagents and methodologies provided herein may be utilized for the following non-limiting exemplary purposes:

1. Proper expression of extreme and hyper-thermophilic genes. The discovery of novel genes from genome sequencing projects has significantly expanded the sources of thermostable enzymes. Total genome sequencing projects of extreme and hyper-thermophiles such as *Sulfolobus sulfactericus, Pyrococcus furiosus, Methanobacterium thermoautotrophicum, Thermus flavus* and others are important for the development of new industrial processes where thermostable enzymes may be utilized.

In order to be a commercially viable enzyme, the enzyme must be capable of being produced and recovered in large quantities in an organism with low cultivation cost. A heterologous host is useful because of the difficulties in growing hyperthermophiles and the lack of systems for cloning and gene analysis for such strains. In one embodiment of the present invention, the host cell is *E. coli*. However, in certain situations, *E. coli* is a sub-optimal host for hyperthermophile gene expression. In several studies, it was shown that certain hyperthermophilic proteins could not assemble properly in *E. coli* (Robb, et al. Gene Discovery and Production of Recombinant Gene Expression in the Marine Hyperthermophile *Pyrococcus furiosus*. The 7th International Symposium on the Genetics of Industrial Microorganisms., Montreal, 1994; Laderman, et al. (1993) a-Amylase from the Hyperthermophilic Archaebacterium *Pyrococcus furiosus*. *J. Biol. Chem.* 268:24402–24407.). In addition, the temperature optima of the proteins being studied are typically too high to permit an analysis of their function in vivo in the mesophilic organism. Thus, in a preferred embodiment, the host cell is from the genus Thermus. Temperature-dependent folding and activity of proteins from hyperthermophiles make species of the genus Thermus a more preferred host for expression of such proteins.

2. Engineered fermentation strains for high-temperature bioprocesses. Many industrial bioprocesses utilize whole-cell fermentation techniques. In many instances, the use of an isolated enzyme system is too expensive or impractical. Many enzymes, such as dehydrogenases that may be utilized to carry out chiral synthesis of pharmaceutical intermediates, require co-factors such as NAD(P) to for their reactions. Cofactors are utilized stoichiometrically during the reaction and must be repeatedly added to the reaction mixture or the reaction must regenerate the cofactor. A whole-cell system provides a alternative for many of these enzymes. Other enzymes may be membrane-bound or require complex subunit or multi-enzyme complexes (such as cytochrome P-450s), allowing for simpler implementation using a whole-cell system. Finally, the synthesis of complex molecules such as steroids, antibiotics, and other pharmaceuticals may require complicated and multiple catalytic pathways. In an isolated system, each step would need to be engineered. In contrast, the organism utilized in a whole cell system provides each of the required pathways. The tools provided herein may be utilized to engineer Thermus with multiple genes, thus providing the organism with the necessary pathways for carrying out such bioprocesses.

In addition, it is often desired to carry out synthetic reactions at high temperatures, because either the reaction is exothermic (therefore cooling is not needed), the substrate or product solubility is greater at higher temperature (which can drastically increase throughput), the viscosity of the reaction is improved (as in the case in many food applications such as the processing of cheese whey), or the reaction proceeds significantly faster at the higher temperature.

3. Genetic thermostabilization of mesophilic genes. The thermolability of most mesophilic proteins can limit their industrial use. It was proposed in the early 1980s that thermostabilization of mesophilic proteins could be accomplished by carrying out activity selections in organisms which grow at high temperatures (Matsumura, et al. (1984) Enzymatic and Nucleotide Sequence Studies of a Kanamycin-Inactivating Enzyme Encoded by a Plasmid from Thermophilic Bacilli in Comparison with That Encoded by Plasmid pUB110. *J. Bacteriol.* 160:413–420; Liao, et al. (1986) Isolation of a thermostable enzyme variant by cloning and selection in a thermophile. *Proc. Natl. Acad. Sci. USA.* 83:576–580). Applicants have developed several directed evolution methods to accelerate the evolution of protein properties such as thermostability through the use of both in vivo and in vitro techniques. Directed evolution relies on a random, but targeted, approach to generating mutations of interest. By carrying out sequential generations of random mutagenesis on a gene of coupled with selection or screening for the resulting proteins, numerous proteins with improved properties have been developed. In each generation, a single variant is generally chosen as the parent for the next generation, and sequential cycles allow the evolution of the desired features. Alternatively, effective mutations identified during one or more generations can be recombined using methods such as 'DNA shuffling' (represented by, for example, sexual PCR). Traits which have been enhanced may include but are not limited to improved substrate specificity, catalytic activity, activity in the presence of organic solvents, expression level and stability.

Liao, et al. ((1986) Isolation of a thermostable enzyme variant by cloning and selection in a thermophile. *Proc. Natl. Acad. Sci. USA.* 83:576–580) first demonstrated in vivo thermostabilization of a gene by using kanamycin nucleotidyl transferase in *Bacillus stearothermophilus* where resistance to 63° C. was shown. To improve the genetic thermostabilization approach, a gene transfer system for Thermus was developed where the upper growth limit was above 80° C. instead of 65° C. as in Bacillus (described in, for example, U.S. Pat. No. 5,786,174 which is hereby incorporated by reference). These experiments were intitially conducted using the thermostabilized kan gene, in which the initial $Km^r$ supported growth only to 55° C. in Thermus and not to 63° C. as reported by Liao, et. al. ((1986) Isolation of a thermostable enzyme variant by cloning and selection in a thermophile. *Proc. Natl. Acad. Sci. USA.* 83:576–580). The regulated expression system provided herein allows for fine-tuning of thermostabilization selection experiments so that the temperature range can be regulated and controlled and cutoff temperatures for selection adjusted in subsequent rounds of mutagenesis. Some important elements of Thermus' genetic background have been previously described. The generation of mutations (Koyama, et al. (1990) Cloning and sequence analysis of tryptophan synthetase genes of an extreme thermophile, *Thermus thermophilus* HB27: Plasmid transfer from replica-plated *Escherichia coli* recombinant colonies to competent *T. thermophilus* cells. *J. Bacteriol.* 172:3490–3495; Koyama, et al. (1990) A plasmid vector for an extreme thermophile, *Thermus thermophilus*. *FEMS Microbiol. Lett.* 72:97–102; Lasa, et al. (1992) Insertional mutagenesis in the extreme thermophilic eubacteria *Thermus thermophilus* HB8. *Molec. Microbiol.* 6:1555–1564), chromosomal integration (Koyama, et al. (1990) Cloning and sequence analysis of tryptophan synthetase genes of an extreme thermophile, *Thermus thermophilus* HB27: Plasmid transfer from replica-plated *Escherichia coli* recombinant colonies to competent *T. thermophilus* cells. *J. Bacteriol.* 172:3490–3495; Koyama, et al. (1990) A plasmid vector for an extreme thermophile, *Thermus thermophilus*. *FEMS Microbiol. Lett.* 72:97–102; Lasa, et al. (1992) Insertional mutagenesis in the extreme thermophilic eubacteria *Thermus thermophilus* HB8. *Molec. Microbiol.* 6:1555–1564), plasmids (Mather, et al. (1990) Plasmid-associated aggregation in *Thermus thermophilus* HB8. Plasmid. 24:45–56; Hishinuma, et al. (1978) Isolation of extrachromosomasl deoxyribonucleic Acids from extremely thermophilic bacteria. *Jour. of General Microbiology.* 104:193–199.), and phages (Sakaki, et al. (1975) Isolation and Characterization of a Bacteriophage Infectious to an Extreme Thermophile, *Thermus thermophilus* HB8. *J.Virol.* 15:1449–1453) have also been studied. Several successful attempts to develop cloning systems using plasmids and chromosomal integration systems were demonstrated (Koyama, et al. (1986) Genetic transformation of the extreme thermophile *thermos thermophilus* and of other thermus spp. *J. Bacteriol.* 166:338–340; Lasa, et al. (1992) Development of Thermus-Escherichia Shuttle Vectors and Their Use for Expression of the *Clostridium thermocellum* celA Gene in *Thermus thermophilus*. *J. Bacteriol.* 174:6424–6431; Mather, et al. (1992) Development of Plasmid Cloning Vectors for *Thermus thermophilus* HB8: Expression of a Heterologous, Plasmid-Borne Kanamycin Nucleotidyltransferase Gene. *Appl. Environ. Microbiol* 58:421–425.). However, none of these provide the versatility as those provided herein.

4. Thermus expression signals. More than twenty genes from Thermus species have been cloned and sequenced (Table 1). However, none of these sequences illustrate the optimal regulatory elements needed to develop a useful system for expression in a thermophile such as Thermus. Applicants have previously documented the nucleotide sequences encoding phosphatases, glycolytic enzymes (β-glucosidases and β-galactosidases), and biosynthetic genes (pyrE, hisB, leuB) from Thermus by complementation of their functions or by testing the specific activities (Weber, et al. (1995) A chomosome integration system for stable gene tranfer into *Thermus flavus*. *Bio/Technology,* Vol. 13(3): 271–275). Expression of these sequences in *E. coli* demonstrated that most Thermus genes are capable of being transcribed in *E. coli*. The comparison of nucleotide sequences from some Thermus genes and operons reveals putative translation initiation signals that are similar to known *E. coli* motifs (Table 1 shows exemplary sequences).

TABLE 1

Putative translation initiation signals of known genes of the genus Thermus

| Organism | Gene | Start codon | RbS | -10 region | -35 region | Ref. |
|---|---|---|---|---|---|---|
| T.aquaticus YTI | L-lactate DH | GTG | n.f. | n.f. | n.f. | (20) |
| | aquaI | ATG | AGGAG | TAGCTT | TTGACA | (21)(22) |
| T.aquaticus B | sucD | GTG | GGAGGTG | n.f. | n.f. | (23) |
| | mdh | GTG | AAGGAG | n.f. | n.f. | (23) |
| T.thermophilus HB8 | tufB | ATG | AGGAGGA | n.f. | n.f. | (24) |
| | tufA | ATG | AGGAGGA | n.f. | n.f. | (25) |
| | icdh | ATG | GGAGG | TGTAGT | TTACAA | (26) |
| | slpA | ATG | AAGGAGGTG | TACGAT | TTGACA | (27) |
| | Xylose isomerase | GTG | AGGAGG | n.f. | n.f. | (28) |
| | gltX | ATG | GAGG | ATAAT | n.f. | (29) |
| | nox | ATG | n.f. | n.f. | n.f. | (30) |
| | 16S RNA | | | TAGCAT | TTGACA | (31) |
| | 23S/5S RNA | | | TATCTT | TTGACA | (31) |
| | NADH dh | | AAGGAGGGG | TAAGAT | TTGCGC | |
| | 4.5S RNA | | | TATACT | TAGCCT | (31) |
| T.thermophilus HB27 | trpB | ATG | AGGGAG | TAGGAT | TTTACC | (11) |
| | trpA | GTG | GGGAGG | n.f | n.f. | (11) |
| T.flavus AT62 | sucB | TTG | AAGGGAGG | TATAAT | n.f. | (32) |
| | sucA | GTG | GGAGG | n.f. | n.f. | (32) |
| | mdh | GTG | AAAGGAGG | n.f. | n.f. | (32) |
| E. coli | | ATG | AAGGAGGTG | TATAAT | TTGACA | |
| | ntsA/intB | | AAGGG | TAGACT | TTGTAG | | n.f. - no homology to *E. coli* found; RbS = ribosome binding site; "-10" and "-35" regions indicate initiator regions.

The expression system provided herein comprises certain genetic elements whose configuration has been manipulated to ensure high levels of protein synthesis in a thermophilic host such as Thermus. In one embodiment, the central element of the expression system is a promoter positioned upstream of a ribosome-binding site, RBS, which is further under the control of a regulatory gene. Provided herein are several exemplary T. thermophilus promoters having activity in T. flavus. In another embodiment, novel promoter regions from bacteria belonging to genus Thermus are provided. In yet another embodiment, a promoter probe vector for Thermus is provided and is useful for evaluating promoter strength.

The isolation of a promoter that functions in a thermophile such as Thermus promoters may be accomplished by generating a library of genomic fragments from the organism by limited restriction digest or other method for generating DNA fragments and inserting the fragments into a reporter vector. As a source for the genomic DNA, one could use any suitable bacterial strain. Preferably, the strain is of Thermus. As an example, in constructing a Thermus promoter library, Thermus chromosomal DNA may be partially digested with a frequent-cutting endonuclease such as Sau3AI and a fraction of the digested fragments having a desired size (for example, approximately 1 kb) purified by any suitable method, such as elution from an agarose gel. These fragments are then ligated with DNA from a reporter vector that has been digested with an appropriate enzyme for ligation to the genomic fragment.

To function properly, the reporter or promoter-probe vector requires the following elements: 1) an E. coli origin of replication (ColEI was used in pGEMtbg); 2) a marker gene, which functions in E. coli (such as the selective drug-resistance marker bla that confers ampicillin resistance); 3) a promoterless reporter sequence; and, 4) a transcriptional terminator (TT) upstream of the reporter gene. Other origins of replication or vector systems, marker genes, reporter genes, and terminators can be used as well to construct similar promoter-probe vectors.

The reporter vector may comprise a plasmid backbone derived from a commonly available vector plasmids including but not limited to pBR322, pBR325, pBR327, pUC 8, pUC 9, pUC 41C, pUC18, pUC19, piz 18, and piz 19. The reporter vector is arranged such that a suitable reporter sequence such as lacZ, tbg, or a drug resistance gene is positioned downstream (or 3') from a polylinker site containing serveral and/or unique restriction enzyme sites. A suitable reporter sequence encodes a gene product detectable via a colorimetric, chromogenic, fluorometric, enzymatic activity or other assay.

A number of genes can be used as either markers to detect insertion of the gene in Thermus or as reporters which can be used to analyze expression in Thermus. Table 2 contains a few examples of such genes, but it should be understood by the skilled artisan that others may also be suitable. Some of these genes confer selectable phenotypes. In this case, media conditions can be established so that only colonies which have expression of these genes activated will grow. Other genes confer phenotypes which can be screened. A screenable phenotype can often yield information about levels of gene expression.

TABLE 2

Marker/reporter genes which can be used in Thermus.

| Marker | Description | Type | Integrative FN | Comments | Ref |
|---|---|---|---|---|---|
| kantr2 | Thermostable kanamycin resistance gene | SEL | + | Works with a variety of promoters and successfully used in promoter-test experiments Expression level effects resistance level in host. | A |
| HLADH | Horse Liver Alcohol Dehydrogenase. | SCR | + | Expression confirmed under control of Leucine promoter in Thermus. Although not from a thermophile, the gene is stable up to about 70° C. Can be quantitated. | B |
| pyrE | Orotodine-5'-phospho-ribosyl-transferase | SEL | + | Selectable marker which can be used as a site of integration in Thermus. | C |
| leuB | Isopropyl malate dehydrogenase | SEL | + | Selectable marker used as a site of integration in Thermus. | D |

Abbreviations: SEL: selectable marker; SCR: screenable marker; ND not determined; FN: Functional.
References: A. U.S. Pat. No. 5,786,174; (Weber, et al. (1995) A chromosome integration system for stable gene transfer into Thermus flavus. Bio/Technology, Vol. 13(3), pp. 271–275). B. U.S. Prov. App. No. 60/046,182 filed May 12, 1997. C. U.S. Pat. No. 5,786,174. D. U.S. Pat. No. 5,786, 174.

The vector may contain more than one reporter sequence located 5' and 3' of the polylinker region. In this manner, the orientation of a promoter region at the polylinker site will not affect expression of the reporter sequence. The genomic fragments are ligated into the polylinker region using standard techniques. In one embodiment, the promoter sequences are amplified by PCR using primers containing, for example, an EcoRI site, −35, −10 and several downstream residues (to include the +1 transcription site). The amplified sequences are then cloned into a TG200 reporter sequence by digesting the PCR fragment with EcoRI and HindIII, followed by subcloning into the pTGeporter vector by digesting the PCR fragment with EcoRI and HindIII.

In a preferred embodiment, a library of T. thermophilus chromosomal fragments is generated by restriction enzyme digestion and cloned into a reporter vector. The reporter sequence is positioned downstream (or 3') of the polylinker region such that insertion of a promoter sequence into the polylinker region will result in expression of the reporter sequence.

Following construction of the reporter vector, the vector may then be transformed into a host cell such as E. coli and screened for promoter activity. Those fragments showing promoter activity in E. coli are then transformed into a thermophile to detect promoter activity in the thermophile. For sequences with promoter activity in E. coli identified from a T. thermophilus chromosomal fragment library, the reporter vector is preferably subsequently transformed into T. thermophilus, and expression of various markers and model enzymes assayed.

In another embodiment, a reporter vector is utilized which has an integrative element capable of driving integration of the reporter sequence into the genome of the host organism.

Preferably, the reporter sequence is positioned in the opposite orientation of the integrative sequences such that occlusion transcription does not occur. As a further safeguard, it is preferable that a transcriptional termination (TT) sequence consisting of a inverted repeat with an A/T region comprising a repeat region for pausing an RNA polymerase where AT serves to separate it from the DNA template, be included in the integration sequence. Similar to the reporter vector described above, the reporter sequence is preferably positioned downstream of a polylinker site into which a putative promoter sequence may be inserted. For example, an integrative vector may comprise portions of the Thermus leuB gene both 5' and 3' of a cassette containing a drug resistance gene adjacent to a putative promoter sequence. If the putative promoter sequence is capable of driving gene expression in Thermus, the host cell will gain resistance to a compound by virtue of expression of the reporter sequence (ie, drug resistance gene) controlled by the putative promoter sequence. The absence of drug resistance indicates that the promoter is not active in Thermus.

In another embodiment, sequencing of the Thermus genome may be performed and putative promoter sequences identified using computerized searching algorithms. For example, a region of a Thermus genome may be sequenced and analyzed for the presence of putative promoters using Neural Network for Promoter Prediction software, NNPP. NNPP is a time-delay neural network consisting mostly of two feature layers, one for recognizing TATA-boxes and one for recognizing so called "initiators", which are regions spanning the transcription start site. Both feature layers are combined into one output unit. These putative sequences may then be cloned into a reporter vector suitable for preliminary characterization in E. coli and/or direct characterization in Thermus.

To optimize the promoter sequence, the length of the promoter sequence can be optimized by performing deletion analysis, such as by using an endonuclease (such as ExoI or Bal31) to create sequential deletions in the promoter sequence or by generating a series of oligonucleotides with shortened sequences from each side of the isolated promoter sequence. The individual deletions can then be tested for activity and expression from each of the promoter regions can be quantitated to determine the minimal sequence needed to confer expression. This minimal promoter region can then be used to express genes of interest in Thermus.

The reagents and methodologies provided herein also provide for the identification of regulated promoters and regulatory elements. By exchanging certain promoter elements from one reporter vector to another using standard molecular biology techniques, specific sequences having certain regulatory effects (ie, increase or decrease expression) on expression of a sequence may be identified. For instance, following identification of a promoter region within a DNA fragment using the techniques described above, certain portions of the promoter may be deleted or excised from the DNA fragment, and the modified promoter re-tested. In the event that expression is observed after this modification, and determination of whether expression has increased or decreased following modification, a positive or negative regulatory element of the promoter may be identified. In addition, specific regions of the putative promoter element may be isolated and tested in isolation. In this manner, specific elements may be identified that regulate gene expression in the host cell. In addition, various regulatory elements identified as described above may be combined into novel promoter sequences. It is also possible to use the techniques described herein to construct hybrid regulated promoters and vectors for regulated expression by combining one or more regulatory elements with a promoter sequences not typically associated with that regulatory elements. The hybrid promoters can then be tested for activity and expression from each of the promoter regions can be quantitated to determine the minimal sequence needed to confer expression. The hybrid promoter region may then be used to express genes of interest in Thermus. Thus, the development of efficient regulated promoters for expression of nucleotide sequence in a thermophile is provided by the instant invention.

Trans-acting regulatory elements may also be identified by screening the libraries in E. coli. As will be understood by the skilled artisan, these elements can be placed on different plasmids and both will remain functional.

The constructs described herein may also be utilized to construct optimal expression systems for the production of industrially important thermophilic model proteins including but not limited to lipases, esterases, hydrogenases, proteases. In addition, the constructs can be utilized to generate bacterial strains with multiple chromosomal insertions and characterize such strains for use in fermentations.

The following Examples are for illustrative purposes only and are not intended, nor should they be construed as limiting the invention in any manner. Those skilled in the art will appreciate that variations and modifications can be made without violating the spirit or scope of the invention.

EXAMPLES

Example 1

Screening a Library of T. thermophilus Chromosomal Fragments for Sequences with Promoter Activity in E. coli A. Assembly of a promoter probe vector for selection of Thermus promoters in E. coli One strategy for discovery of Thermus promoters is to first identify a promoter from Thermus which functions in an intermediate strain, such as E. coli, and then test the promoters which have been identified in Thermus. Performing this two-step process can potentially dissociate the promoter from a regulatory element and help identify Thermus promoters that may be tightly controlled.

For primary selection of Thermus chromosomal fragments exhibiting promoter activity in E. coli, the promoter probe vectors pGEMtbg and pVUF10tbg (FIG. 1) were constructed. The promoter-probe vectors utilized herein include: 1) an E. coli origin of replication (ColEI was used in pGEMtbg); 2) a marker gene which functions in E. coli (the selective drug-resistance marker bla conferring ampicillin resistance was used in pGEMtbg); 3) a promoterless reporter gene (tbg was used in pGEMtbg); and, 4) a transcriptional terminator (TT) upstream of the reporter gene.

In the construction of pGEMtbg, the tbg gene of T. aquaticus encoding Thermo-β-galactosidase (Tbg) was used as a reporter sequence. Tbg expression can be detected using several possible chromogenic substrates such as 5-Bromo-4-Chloro-3-indolyl-β-D-galactopyranoside (X-Gal) and 5-Bromo-4-Chloro-3-indolyl-β-D-glucopyranoside (X-Glc) to identify clones exhibiting B-glucosidase (or B-galactosidase) activity. Expression of E. coli β-glucosidase and β-galactosidase activities are tightly controlled under uninduced conditions. In addition, the background activity of the endogenous enzyme is insufficient to turn colonies blue and E. coli lacZ β-galactosidase mutants are common. Tbg also demonstrates thermostability, which facilitates assay of the enzyme's activity in crude cell lysates. Heating of lysates for 15 minutes at 65° C. totally inactivates endogenous activity, making the detection of low activities of Tbg possible. To incorporate the tbg gene into pGEM, it was amplified by PCR.

The tbg gene was isolated from a preparation of *Thermus aquaticus* genomic DNA. Primer sequences used for the PCR amplification of the tbg gene to construct pGEMtbg included primer 187 which contained a PmlI, BstEII restriction sites followed by the trp transcriptional terminator (underlined) followed by BclI, SnaBI, NheI, FscI, AvrII restriction sites, followed by a sequence homologous to the 5' end of the tbg gene (bold) started with a putative ATG site as depicted below. Primer 227 contained sequence homologous to the 3' end of the tbg gene.

187    5'-CACGTGGTTA    CCCGCCTAAT GAGCGGGCTT TTTTTTGATC ATACGTAGCT AGCCCCGGCC GGCCTAGGAT GGCAATTATT CAATTTC-3' (SEQ ID NO: 1)

227 5'-TTAATATTCA AACCATTTAT TTTCTAT (SEQ ID NO: 2)

The 5' end primer was designed so that tbg, upstream of the Shine-Delgarno (SD) site, had unique SnaBI and BclI sites for cloning blunt-ended DNA fragments and fragments obtained as a result of partial digestion with Sau3AI. The strong transcription terminator of *E. coli* trp operon was included upstream of the cloning sites. The PCR fragment was subcloned into the pGEM-T vector (obtained from Promega) to generate pGEMtbg using standard techniques. pGEM-T allows direct cloning of PCR products without the need for restriction digestion. Clones with the proper orientation of the gene were determined by restriction analysis.

Plasmid pVUF10tbg (FIG. 1) was constructed by inserting the kanamycin drug resistance marker kantr2 (Weber, et al. (1995) A chomosome integration system for stable gene tranfer into *Thermus flavus*. Bio/Technology, Vol. 13(3): 271–275) into the Nde I to Not I site of pGEMtbg. The fragment containing the kanamycin gene was prepared by amplification with primers 388 and 442 listed below. The fragment was digested with NotI and NdeI and cloned into pGEM-tbg which had also been digested with NdeI and NotI.

442 Containing the Nde I (bold), NstEII, and PmlI site followed by homology to the kanamycin gene:
    5'TGGTTACCAT ATGGTAACCA CGTGAATGGA CCAATAATAATG (SEQ ID NO: 3)

388 Containing the NotI site (bold) followed by the rrnC transcriptional terminator (underlined) and homology to the kanamycin gene:
    5'GTTATCTGAAAGCGGCCGC TTTCAGATAAAAAAAATCCTTAGCT TTCGCTAAGGATGGATTTCTGGCTCA AAATGGTATGGTTTTGAC-3'(SEQ ID NO: 4)

The resultant PCR fragment was then isolated and inserted into pGEMtbg plasmid using standard molecular biology techniques.

B. Construction and screening of a *T. thermophilus* genomic library in *E. coli*

To construct a Thermus promoter library, *T. thermophilus* chromosomal DNA was partially digested with Sau3AI and a fraction of the digested fragments of 1 kb size were purified by elution from an agarose gel. These fragments were then ligated with DNA from the pVUF10 cloning vector which has been digested with BclI for cloning. *T thermophilus* was used as the source of genomic DNA since the *T. thermophilus* and *T. flavus* strains utilized are highly related, but not identical. The ligated DNA was used to transform *E. coli*. Transformed cells were cultured on LB agar containing X-glc at 50 µg/ml, and cultured for several days at 37° C. Recombinant clones exhibiting promoter activity (approximately one percent of all recombinant clones) developed color of different shades of blue due to tbg. Out of several hundred of blue colonies, 24 were randomly selected for further analysis.

The nucleotide sequences of each insert was determined. The entire insert was sequenced for clones VV12, VV18, VV51 and VV57 and about 50% of the sequence was determined for the remaining clones. The sequences of clones 1 and 2 overlapped and were combined resulting in the sequence designated VV1-2. Computer analysis of these sequences using BLASTN search algorithm revealed putative core promoter regions showing similarity to the consensus promoter sequence of *E. coli* (Table 3). Sequence analysis of promoter VV1-2 revealed two inverted repeats, one of which was at the transcription-start site. These sequences were AT-rich (below 40% GC) compared with the GC-rich content of random Thermus DNA which is about 72% GC. This preliminary search was performed using Sequencher DNA assembler (commercially available). One of these potential promoters matched the known promoter for *T. thermophilus* chaperonin (FIG. 3).

TABLE 3

Promoters identified from homology search

| Sequence | clone |
|---|---|
| TTGACATTCCCCCCGCCCCGGGGTACCCTCCTTCCCGGGAGGCGCGCCTCCCGAGGAGAACGGTACCCATG.. | VV1-2 (SEQ ID NO: 5) |
| TTGACAAGGGAAAGCCGGGGTGCTAACTTAGGGATTGCGCTGCCCT... ...ATACGTAGCTAGCCCCGGCCGGCCTAGGATG... | VV57 (SEQ ID NO: 6) |
| TTTATTCGCAAAGCCCCCCGGTGCTATAATGGAAGACGGCGTCTAAACGCCTTCTAGGAGCGCTATG... | VV34 (SEQ ID NO: 7) |
| TTGACGCTCCCCCAAAAGCCCCCTTATAATCGCTGTGGAATAGCTTCCAAAGGAGGTACGGTATG... | VV40 (SEQ ID NO: 8) |
| TTGTAGAGGCGGCGCTCCGCCTCTATGGCCACCCGGATCATTTACCCCCTCATCAAGGCCACC... | VV37 (SEQ ID NO: 9) |
| TTGACAAAGGCCATGCCTCCTTGGTATCTTCCCTTTTGCGCTGCCCTGAGGGGG... | VV53 (SEQ ID NO: 10) |

TABLE 3-continued

Promoters identified from homology search

| Sequence | clone |
|---|---|
| TTGACAAGGTCTTCCGCCAGGCCTCCATCCACCACGTCATCGTCCTGGAG... | VV18 (SEQ ID NO: 11) |
| TTCGAATCCCTCCGGGCCCGCCATTGTTATCTTGGAAATGGGTAGCCTTT... | VV51 (SEQ ID NO: 12) |

ATG Start Codons shown in bold font are verified real start codons as identified by "CodonUse" which looks for codon usage patterns in open reading frames. "clone" denotes promoter clone name. Putative SD, translation start, -35 and -10 sites are shown in bold.

To determine the promoter activity in each of the clones, a Tbg assay was performed, as shown in Table 4 below. As shown therein, expression from the promoters varies.

TABLE 4

Expression characteristics of the cloned promoter candidates

| Promoter Clone | E. coli Average Units | Temp. Induction 42° C./30° C.* | Homologies & Comments |
|---|---|---|---|
| VV1 | 186 ± 9 | 1.1 | |
| VV2 | 36 + 24 | 1.6 | none |
| VV4 | 152 ± 23 | 1.4 | Thermus NADH dh, DNA pol |
| VV7 | 120 ± 39 | 1.2 | none- |
| VV12 | 132 ± 23 | 1.4 | |
| VV13 | 350 ± 13 | 2.1 | |
| VV15 | 150 ± 8 | 1.7 | glutamate synt, Thermus dh, def, fmt, proC |
| VV18 | 97 ± 2 | 1.3 | |
| VVHC1 | 287 ± 16 | 1.6 | |
| VV31 | 5836 ± 511 | 1.6 | |
| VV32 | 67 ± 15 | 1.4 | B. sp wap, licT |
| VV33 | 87 ± 20 | 1.0 | |
| VV34 | 66 ± 21 | 1.5 | 23S rRNA*** |
| VV35 | 81 ± 16 | 1.3 | fus??? |
| VV36 | 40 ± 12 | 1.3 | Ile-tRNA synthetase |
| VV37 | 62 ± 8 | 1.4 | Thermus slp, nox, pol, Zea rbd inac |
| VV38 | 59 ± 9 | 1.6 | Thermus lysyl tRNA synthetase |
| VV39 | 65 ± 6 | 1.4 | ribosomal spacer |
| VV40 | 118 ± 10 | 1.2 | mus munculus transcription factor |
| VV47 | 95 ± 24 | 1.1 | |
| VV51 | 210 ± 4 | 1.4 | |
| VV53 | 149 ± 33 | 2.0 | |
| VV57 | 56 ± 27 | 2.1 | T. thermophilus Chaperonin |
| VV70 | 134 ± 11 | 1.1 | T. thermophilus ribonucleaseH |
| VV1.2 | 2000 ± 242 | nd | Tbg with promoter |

Assays were performed as described for β-galactosidase in Miller (Miller, J. H. A short course in bacterial genetics, Cold Spring Harbor Laboratory Press, Cold Spring Harbor. 1992) using o-nitrophenyl galactopyranoside (ONPG) as a substrate modified to be run at 65° C. to assay for Tbg.
*Ratio of expression from E. coli host grown at 42° C. divided by E. coli host grown at 30° C.

The promoters were then assayed at higher temperatures in E. coli. While a temperature sensitive repressor cloned along with the promoter was unexpected, although possible, temperature dependence of the promoter could potentially be observed because DNA from Thermus is typically GC rich. In addition, it was also possible that the promoter would cross-react with E. coli regulatory elements. Three of the promoter clone candidates showed twice the level of expression at 42° C. Clone VV57 appears to have homology to a Thermus heat shock protein (actually a chaperonin) as is shown in FIG. 3.

Example 2

Integrative Promoter-Identification Vector for Thermus

To evaluate strength of the identified core promoter regions in Thermus, a novel integrative promoter test vector was constructed for use in T. flavus. The vector was constructed to include a thermostable kanamycin resistance gene (kan$^{tr2}$), which had been previously demonstrated to function in Thermus. The vector integrates by a double-crossover event so the insertion is stable and permanent. The integrative vector pTG100kan$^{tr2}$ for use in T. flavus is a suicide vector having the Km$^R$ gene as a selective marker, and a leuB as a region of homology where integration into the chromosome occurs (Weber, et al. (1995) A chomosome integration system for stable gene tranfer into Thermus flavus. Bio/Technology, Vol. 13(3): 271–275). Other such reporter genes and insertion sites could be used as well.

Figure 3B:
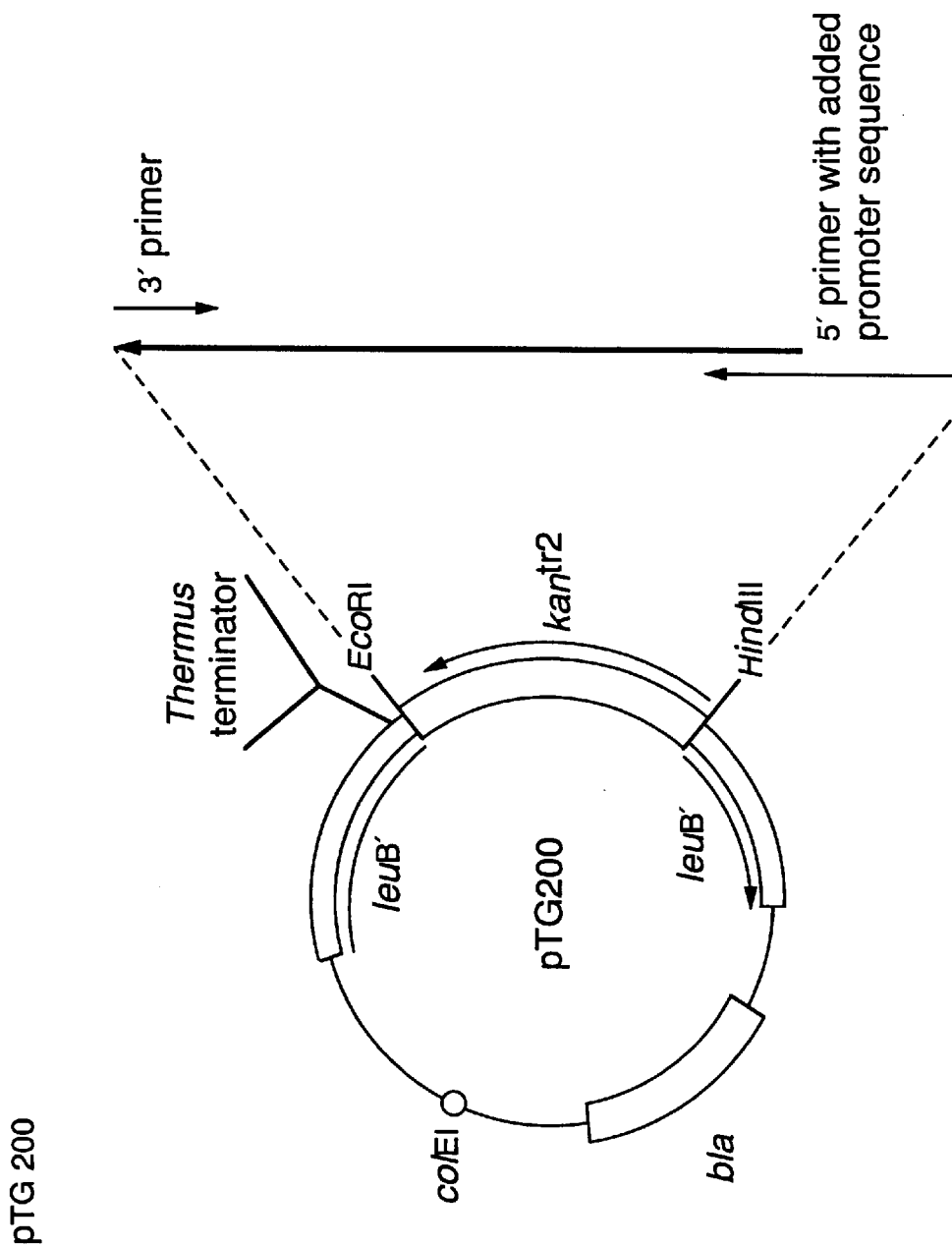
FIG. 3. Construction of pTG200 and development of promoter test vectors. A) Comparison of terminator sequences from Thermus SEQ ID NO: 47–SEQ ID NO: 52. The his terminator was used in the construction of pTG200. B) pTG200 consists of an *E. coli* shuttle vector with the Thermus leuB gene disrupted by the promoterless kantr2 gene in the opposite direction. A strong Thermus transcription terminator is placed downstream of the kantr2 gene to prevent transcription through the gene in the opposite direction. Promoter-test vectors were constructed by using primers to the two ends of the kan gene with an extended 50–60 bp promoter attached at the 5'end.

A promoter-test vector was redesigned from pTG100kan$^{tr2}$ (Weber, et al. (1995) A chomosome integration system for stable gene tranfer into Thermus flavus. Bio/Technology, Vol. 13(3): 271–275). In a novel vector, pTG200, the promoterless Km$^R$ gene was utilized as a reporter gene (FIG. 3B). In this vector, Km$^R$ is oriented in the opposite direction to leuB. Therefore, upon integration of a fragment bearing a promoter in front of Km$^R$ into the T. flavus chromosome, simultaneous transcription from the leu and Km$^R$ promoters might cause occlusion transcription, which is a phenomenon observed when transcription through promoter inhibits promoter's function. To avoid such interference, the Thermus transcriptional terminator was inserted downstream of the Km$^R$ gene. A consensus sequence of Thermus transcriptional terminator was derived by analysis of a number of Thermus terminators as shown in FIG. 3A. In this example, the sequence below was used as a terminator (underlined sequences signify the regions of inverse homology):

TGCCA<u>CCCCATGCTGGC</u>TTGC<u>GCCAGCATGGGG</u>CCCCGGCAAAAGAATTC (SEQ ID NO. 13)

Positioning the promoterless Km$^R$ gene in the opposite direction to leuB, pTG200 did not confer Km$^R$ to *T. flavus* cells and, therefore, could be used as a promoter probe vector.

The terminator sequence was derived by a comparison of terminators shown in FIG. 3A and using the his terminator as a model. A terminator sequence was obtained as a part of a larger fragment amplified by PCR using the following primers:

TR5KAN—Containing NcoI site, transcriptional terminator (underlined), EcoRI site, and 5' end sequence of the KmR gene:

```
5'-acacacacacaCCATGGcctaa TGCCA CCCCATGCTGGCTTGC
            NcoI           ------terminator-----

GCCAGCATGGGGCCCCGGCAAAA GAATTCaaagggaatgagaatagtgaatggacc-3'     (SEQ ID NO: 14)
-----------terminator--- EcoRI------5'end of KmR gene-----

KAN3- Containing PstI and HindIII sites and 3'portion of the Km gene
5'-gagcatggccCTGCAG AAGCTT caaaatggtatgcgttttgacacatcca-3'        (SEQ ID NO: 15)
           PstI HindIII -----3'end of KmR gene-----
```

A DNA fragment obtained by PCR amplification of the KmR gene from pTG100 was digested with PstI and NcoI and subcloned into the pTG100 cleaved with NcoI and NsiI.

It turned out that the terminator diminished transcription but did not terminate it completely so that we could observe weak growth of *T. flavus* on Kmtransformed with the plasmid described above. To avoid this effect, we inverted the kanamycin gene in the construct. To invert the gene, we amplified it by PCR using primers 3KM-RI and 5KM-H3 to obtain a DNA fragment bearing promoterless KmR gene:

```
5'-acacacGAATTCcaaaatggtatgcgttttgacacatcc-3'        (SEQ ID NO: 16)
         EcoRI 5'-cacacacaAAGCTTtacgtatctagagggaatgagaatagtgaatggacc-3'  (SEQ ID NO: 17)
         HindIII
```

The fragment was cleaved with EcoRI and HindIII and subcloned into the described above plasmid cleaved by the same enzymes to give pTG200. The resulting plasmid has a promoterless KmR gene with a unique HindIII site upstream and a terminator downstream. We did not observe growth of Thermus cells transformed with pTG200 on Km plates. Hence, the plasmid can be used as a promoter probe vector in Thermus.

To check activity of the promoters identified in *E. coli*, the core regions attached to the kanamycin resistance gene were amplified by PCR using primer 3KM-RI and one of the following primers:

VV37KM
acacacAAGC Ttgtagaggc ggcgtccgc ctctatggcc acccg- gatca tttaccccct catcaaggag gagaatagtg Aatggaccaa taatgac (SEQ ID NO: 18)

VV53KM
acacacacAA GCTTgacaaa ggccatgcct ccttggtatc ttc- ccttttg cgctgccctg aggaggagaa tagtgaatgg accaataata atgact (SEQ ID NO: 19)

VV18KM
acacacacAA GCTTgacaag gtcttccgcc aggcctccat ccac- cacgtc atcgtcctgg aggaggagaa tagtgaatgg accaataata atgact (SEQ ID NO: 20)

VV51KM
acacacAAGC Ttcgaatccc tccgggcccg ccattgttat cttg- gaaatg ggtagccttt aggaggagaa tagtgaatgg accaataata atgact (SEQ ID NO: 21)

VV57KM
acacacacAA GCTTgacaagg gaaagccggg gtgctaactt agggattgcg ctgccctcat acgtaggagg agaatagtga atggac- caat aataatgac (SEQ ID NO: 22)

VV12D2 PRIMER
acacacacAA GCTTgacatt cccccccgccc cgccgtaccct cct- tcccggg aggaggagaa tagtgaatgg accaataata atgactag (SEQ ID NO: 23)

All PCR reactions were performed in a volume of 100 microliters. The reaction mixture contained 50 mM KCl, 10 mM TrisCl pH 8.3, 1.5 mM MgCl$_2$, 0.2 mM dNTPs (A, C, G, T), 2 U Taq DNA polymerase (Perkin-Elmer), 40 pmole of each primer, 100 ng of template DNA. The thermalcycler repeated the following steps for 30 cycles: 1 minute at 94° C., 1 minute at 55° C., 1 minute at 72° C. PCR fragments were cleaved by HindIII and EcoRI and subcloned into pTG200 cleaved by the same enzymes. DNA of the resulting plasmids was used to transform *T. flavus*. Transformed cells were plated on LB agar containing 20 µg/ml Km.

Promoter VV1-2 was also modified by removal of the larger or both inverted repeats because it appeared that this inverted repeat might effect ribosome binding. Putative core promoters were placed immediately upstream of the Km$^R$ gene and integrated into the *T. flavus* chromosome. Promoters VV1-2/D2, VV40, VV53, and VV57 proved functional in *T. flavus*, conferring Km resistance to the cells upon transformation at 20 µg/ml. It is possible that the other promoters may confer resistance below this level, however as the level of kanamycin drops to about 10 µg/ml, background growth of Thermus begins to occur. The unmodified VV1-2 without the inverted repeat removed did not give expression when tested, in contrast to VV1-2/D2 which gave the strongest expression.

VV1-2 TTGACATTCCCCCCGCCCCGGGGTAC-CCTCCTTCCCGGGAGGCGCGCCTCCCGA GGAGAA (SEQ ID NO: 24)

VV1-2/D2 TTGACATTCCCCCCGCCCCGGGGTAC-CCTCCTTCCCGGGAGGAGGAGAA (SEQ ID NO: 25)

FIG. 4. Removal of hairpin loop region in VV1-2 promoter. The −35, −10 and SD regions are shown in bold. The inverted repeat is underlined.

To confirm integration of the Km$^R$ gene into the *T. flavus* chromosome had occurred in the strains from transformants were obtained, Southern hybridization and PCR analysis of the promoters was performed. The data indicates that integration of Km$^r$ into leuB had occurred. To estimate activity of the promoters, clones were cultured on TT agar plates containing various amounts of Km. The data indicated that the modified VV1-2 was the most active of the tested promoters, conferring to the cells resistance of up to 1000 μg/ml Km (Table 5). While high levels of kanamycin resistance had been reported on multicopy plasmids in other organisms, stable resistance to kanamycin at these levels had not been previously observed in Thermus.

selection or screening for promoter sequences which activate the reporter gene.

To confirm integration of the $Km^R$ gene into the *T. flavus* chromosome has occurred in the strains from which the transformants are obtained, Southern hybridization and PCR analysis of the promoters is performed. The nucleotide sequences of the putative promoter sequences is then determined by sequencing the Thermus genomic fragment. Com-

TABLE 5

Ability of the tested promoters to confer kanamycin resistance on a promoterless kantr2 gene in Thermus

| Plasmid-promoter | Initial Transformation at 20 μg/ml Kanamycin | Kanamycin resistance at higher levels* | | | | | | |
|---|---|---|---|---|---|---|---|---|
| | | 50 μg/ml | 100 μg/ml | 200 μg/ml | 400 μg/ml | 600 μg/ml | 800 μg/ml | 1000 μg/ml |
| pTG200-none | − | | | | | | | |
| pTG200-VV1-2 | − | | | | | | | |
| pTG200-VV1-2/D2 | + | + | + | + | + | + | + | + |
| pTG200-VV57 | + | + | + | + | − | − | − | − |
| pTG200-VV34 | − | | | | | | | |
| pTG200-VV40 | + | + | + | + | + | + | + | − |
| pTG200-VV37 | − | | | | | | | |
| pTG200-VV53 | + | + | + | + | + | + | − | − |
| pTG200-VV18 | − | | | | | | | |
| pTG200-VV51 | − | | | | | | | |

*The transformants were tested on TT-Agar plates with the corresponding amounts of kanamycin added.

Example 3

Integrative Promoter-Identification Vector for Thermus

Promoters are selected by direct cloning and of libraries into a Thermus strain as well. This method avoids the initial characterization of promoter activity in *E. coli*. Construction of a Thermus promoter library for direct transformation in Thermus is carried out utilizing a screening or selection marker that functions in Thermus. This marker is incorporated into a promoter probe vector capable of either integrating into the Thermus chromosome or being maintained extrachromosomally on a suitable plasmid in Thermus. A vector such as the promoter-test vector pTG200 (described above, Example 2) is one such vector. In this case, the promoterless $Km^R$ gene is utilized as a reporter gene (FIG. 3B).

In order to use the promoter probe vector, Thermus chromosomal DNA is partially digested with a frequent-cutting endonuclease (such as Sau3AI) and a fraction of 1 kb fragments are purified by elution from an agarose gel. These fragments are then ligated with DNA from the promoter-test pTG200 vector which has been digested with an appropriate enzyme (BclI) for cloning. The ligated DNA is then used to transform Thermus. The plating media contains a suitable amount of the selection (or screening) agent such as kanamycin in this example, which is determined by testing a series of concentrations and choosing one just strong enough to prohibit growth of untransformed strains. This allows puter analysis of these sequences using BLASTN search algorithm is then utilized to reveal putative core promoter regions. The promoter strength of the discovered promoters is then analyzed using the methods described in Example 2 using either the same or a different reporter gene.

Example 4

Putative Promoters from *T. flavus*

To date, approximately 300 kb comprising about 20% of *T. flavus* genome has been sequenced by the applicants. A search for putative promoters within these sequences has been accomplished using Neural Network for Promoter Prediction software, NNPP. NNPP is a time-delay neural network consisting mostly of two feature layers, one for recognizing TATA-boxes and one for recognizing so called "initiators", which are regions spanning the transcription start site. Both feature layers are combined into one output unit.

Nineteen putative promoters were identified in the 25 kb contig by NNPP (Table 6). Though a basis for a search by NNPP is −10 and +1 regions, −35 boxes which were found for most of identified promoters match consensus sequence TTGNCN derived from published data and from data obtained in the experiments described herein.

TABLE 6

Putative Promoter Sequences Predicted for *T. flavus* contig TF4-6-10.1

```
                          -35                           -10
             ATGGCATTGTCTTTCCGCTATTGAATGACTATCATTCAAGTATGGAAAGA    (SEQ ID NO: 26)
```

TABLE 6-continued

Putative Promoter Sequences Predicted for *T. flavus* contig TF4-6-10.1

| Sequence | ID |
|---|---|
| GAGGTTGCTTGGTTCCGGTGCACGAGTTCTATTCTGCCCAGGCCGTAGCG | (SEQ ID NO: 27) |
| GAGTACGTTGACCAGCGCTCCCCGAAAGGTATAAGCGGGCACGTAAAGCC | (SEQ ID NO: 28) |
| ACCTTGTCGTGCCTCGCCTTGAGGTAGAGGAACATGGCGTAGGGCTCCTG | (SEQ ID NO: 29) |
| CTAATCTGGAAGTAGGCCGGGTTCTTGGCGATGATCTCCCACACCAGCAC | (SEQ ID NO: 30) |
| GACTTGCAGAAACTTTTGGTAACCTGCCATAGCTTCTACCCTCCTCGTTC | (SEQ ID NO: 31) |
| TTTGTTAAAGGAAGCGAGCTTTCCTCGCACATAATTCACCAGATTCAAAT | (SEQ ID NO: 32) |
| GCTCGCTTCCTTTAACAAAGGTGATCCGGTACTAAAAAATCTGCAAGAGG | (SEQ ID NO: 33) |
| AACACGCATCTGATTGGCAGACCTTTTTCCAGAATATTGTTGAAGACCGT | (SEQ ID NO: 34) |
| TATGACCGTGGATGAAGTCAGTACCTGGCCGCGGTCTTATGGGCACCTGG | (SEQ ID NO: 35) |
| GCAATCAGAATGTCAAGCAAAAATTGGAGTCGCTCAAAATCCCCGACTCC | (SEQ ID NO: 36) |
| CAGGTCTAGTTTGGCGACGCGAGGCTCAAGGGAATACCGTCCCGGACCGC | (SEQ ID NO: 37) |
| TTGGTTGGTGTCTTCGGCCAGAAAAGGGAAATAATCCCAGGTCATGCCC | (SEQ ID NO: 38) |
| AACTGGTTTGAGGCGGCGCTTCATCTCGTCAAAGTCCACCAATCCCGGCT | (SEQ ID NO: 39) |
| GAAGTTTTGTAGCGAGACCCAAGAGAAATCATGATATGAGTGTGGTACTT | (SEQ ID NO: 40) |
| GGGAGGCCATCTTGTCTGGATTGTAGCACTTCCCTATCCTTAGCCCAAGG | (SEQ ID NO: 41) |
| GTGCGCCTATTTTGAGTTCTGCTTCGTGGAGGAGGAAGATGGCTAAGCCG | (SEQ ID NO: 42) |
| ACCCCGGGGGTTGACGCACACCCCCGATCTGCTAACTTGGCCTTAAGT | (SEQ ID NO: 43) |
| GACCAACAGCCATTGGCGCAAAGTACCACACTCATATCATGATTTCTCTT | (SEQ ID NO: 44) |

The putative promoter sequences of SEQ ID NO: 26–44 are amplified by PCR using primers containing restriction sites compatible with the restriction sites available for cloning 3' of the kanamycin sequence of the promoter-test vector pTG200. These fragments are then ligated with DNA from the promoter-test pTG200 vector which has been digested with an appropriate enzyme for cloning. The ligated DNA is then used to transform Thermus. The plating media contains a suitable amount of the selection (or screening) agent such as kanamycin in this example, which is determined by testing a series of concentrations and choosing one just strong enough to prohibit growth of untransformed strains. This allows selection or screening for promoter sequences which activate the reporter gene. To confirm integration of the $Km^R$ gene into the *T. flavus* chromosome has occurred in the strains from which the transformants are obtained, Southern hybridization and PCR analysis of the promoters may be performed. Computer analysis of these sequences using BLASTN search algorithm may then be utilized to reveal putative core promoter regions. The promoter strength of the discovered promoters may then be analyzed using the methods described in Example 2 using either the same or a different reporter gene.

Example 5

Promoter Optimization for Gene Expression in a Thermophile

To optimize the promoters found to be useful in driving gene expression in a thermophilic organism, promoter deletions constructs are generated.

A. Promoter Optimization by PCR

One method to generate sequential deletions is by PCR amplification. A 1 kb thermophile genomic fragment that is observed to drive gene expression in a thermophilic organism is modified to generate subfragments at 100 nucleotide intervals by PCR. PCR primers are designed that correspond to regions of the 1 kb fragment as follows: bp 1–900, bp 1–800, bp 1–700, bp 1–600, bp 1–500, bp 1–400, bp 1–300, bp 1–200, and bp 1–100. The primers also incorporate restriction enzyme sites suitable for insertion into pTG200 reporter vector.

B. Promoter Optimization using an Exonuclease

Exonucleases such as Exo III or Bal31 may also be used to generate sequential deletions of the promoter regions. These enzymes are employed using standard molecular biology techniques or as described by supplier of these enzymes (New England Biolabs) to generate a series of random deletions by reacting with a linearized plasmid or fragment of DNA. The exonucleases generate a time-dependant set of deletions from one or both ends of the linear DNA. In the case of Bal31, deletions at both ends of the linear fragment that has been treated are obtained and the deleted promoter sequence subcloned into an appropriate test plasmid such as pTG200. In order to do this, the deletion ends are repaired with Mung Bean Nuclease so that they are suitable for subcloning, digested with an appropriate restriction endonuclease which can be used to isolate the remaining promoter fragment, and religating into the test plasmid. In the case of exo III, it is possible to obtain deletions at only one end (for example the end of the linearized plasmid containing the promoter sequence) if appropate set of restriction endonucleases are used. Several kits are available to do this (such as the Exo-Size™ kit from New England Biolabs). Exo III prefers digestion of DNA which contains a blunt or 3' recessed ends, so if two appropriate endonucleases can be used to linearize the plasmid, then after repairing the deleted ends to make them suitable for cloning with Mung Bean Nuclease and optionally adding a linker DNA, the DNA can be directly religated and used for testing without the need for subcloning. The DNA from either method can be transformed into E. coli and a series of plasmids containing a series of deletion constructs from each end of the putative promoter can be identified.

C. Testing the Constructs

Following promoter modification as described above, constructs containing one or more of the various subfragments are made using standard molecular biology techniques such that each subfragment has the potential to drive expression of the kanamycin resistance gene following transformation of the thermophile with the ligated reporter vector. The thermophilic organism is then assayed for kanamycin resistance by plating on kanamycin-containing plates. Growth in the presence of increasing amounts of kanamycin indicates that the subfragment is active in the thermophilic organism.

Following identification of those subfragments having activity in the thermophile, the fragments may be combined by ligation or PCR amplification and co-inserted into pTG200 or another reporter vector. The ability of these combined subfragments to drive gene expression in the thermophile is then determined by the presence or absence of growth in the presence of kanamycin. In this manner, it is possible to identify those fragments that function additively or synergistically to drive high expression in the thermophile.

We claim:

1. A recombinant expression vector comprising a thermophile promoter, said promoter comprising a DNA sequence selected from the group consisting of SEQ ID NO: 5, SEQ ID NO: 6, SEQ ID NO: 7, SEQ ID NO: 8, SEQ ID NO: 9, SEQ ID NO: 10, SEQ ID NO: 12, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, and SEQ ID NO: 44.

2. The recombinant expression vector of claim 1 wherein the thermophile promoter sequence is operably linked to a reporter sequence.

3. The recombinant expression vector of claim 1 wherein the thermophile promoter sequence is operably linked to a nucleic acid sequence encoding a protein.

4. An isolated DNA molecule comprising the thermophile terminator sequence of SEQ ID NO: 13.

5. A recombinant expression vector comprising:
   a) a coding sequence encoding a protein;
   b) a thermophile promoter selected from the group consisting of SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, and SEQ ID NO: 44 operatively linked to said coding sequence to form a promoter/coding sequence cassette;
   c) a drug resistance marker; and,
   d) a 3' and a 5' DNA targeting sequence that are together capable of allowing integration of the promoter/coding sequence cassette into the genome of a thermophile;
   wherein said promoter/coding sequence cassette is flanked by said 3' and said 5' DNA targeting sequences; and, said promoter/coding sequence cassette is positioned in the opposite orientation of the DNA targeting sequences.

6. A method for expressing a protein in a bacterium of the genus Thermus comprising transforming into the bacterium the recombinant expression vector of claim 5 wherein the promoter/coding sequence cassette is stably integrated into the genome of the bacterium and culturing the transformed bacterium under culture conditions wherein the protein is expressed.

7. A host cell having the promoter/coding sequence cassette of claim 5 stably integrated into its genome such that expression of the protein occurs within the host cell.

8. A recombinant expression vector comprising a thermophile promoter wherein the thermophile promoter comprises SEQ ID NO: 11 and wherein the thermophile promoter sequence is operably linked to a reporter sequence.

9. A recombinant expression vector comprising a thermophile promoter wherein the thermophile promoter comprises SEQ ID NO: 11 and wherein the thermophile promoter sequence is operably linked to a nucleic acid sequence encoding a protein.

* * * * *

SEQUENCE LISTING

```
<160> NUMBER OF SEQ ID NOS: 52

<210> SEQ ID NO 1
<211> LENGTH: 87
<212> TYPE: DNA
<213> ORGANISM: Artificial Sequence
<220> FEATURE:
<223> OTHER INFORMATION: Description of Artificial Sequence: PCR primer
      187

<400> SEQUENCE: 1
cacgtggtta cccgcctaat gagcgggctt tttttgatc atacgtagct agccccggcc      60
ggcctaggat ggcaattatt caatttc                                         87

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: PCR primer
      227

<400> SEQUENCE: 2
ttaatattca aaccatttat tttctat                                         27

<210> SEQ ID NO 3
<211> LENGTH: 42
<212> TYPE: DNA
<213> ORGANISM: Artificial Sequence
<220> FEATURE:
<223> OTHER INFORMATION: Description of Artificial Sequence: PCR primer
      442

<400> SEQUENCE: 3
tggttaccat atggtaacca cgtgaatgga ccaataataa tg                        42

<210> SEQ ID NO 4
<211> LENGTH: 88
<212> TYPE: DNA
<213> ORGANISM: Artificial Sequence
<220> FEATURE:
<223> OTHER INFORMATION: Description of Artificial Sequence: PCR primer
      388

<400> SEQUENCE: 4
gttatctgaa agcggccgct ttcagataaa aaaaatcctt agctttcgct aaggatggat     60
```
ttctggctca aaatggtatg gttttgac                                              88

<210> SEQ ID NO 5
<211> LENGTH: 71
<212> TYPE: DNA
<213> ORGANISM: Artificial Sequence
<220> FEATURE:
<223> OTHER INFORMATION: Description of Artificial Sequence: VV1-2
      promoter sequence

<400> SEQUENCE: 5
ttgacattcc ccccgccccg gggtaccctc cttcccggga ggcgcgcctc ccgaggagaa          60
cggtacccat g                                                              71

<210> SEQ ID NO 6
<211> LENGTH: 76
<212> TYPE: DNA
<213> ORGANISM: Artificial Sequence
<220> FEATURE:
<223> OTHER INFORMATION: Description of Artificial Sequence: VV-57
      promoter sequence

<400> SEQUENCE: 6
ttgacaaggg aaagccgggg tgctaactta gggattgcgc tgcccttacg tagctagccc          60
cggccggcct aggatg                                                         76

<210> SEQ ID NO 7
<211> LENGTH: 67
<212> TYPE: DNA
<213> ORGANISM: Artificial Sequence
<220> FEATURE:
<223> OTHER INFORMATION: Description of Artificial Sequence: VV34
      promoter sequence

<400> SEQUENCE: 7
tttattcgca aagcccccg gtgctataat ggaagacggc gtctaaacgc cttctaggag           60
cgctatg                                                                   67

<210> SEQ ID NO 8
<211> LENGTH: 65
<212> TYPE: DNA
<213> ORGANISM: Artificial Sequence
<220> FEATURE:
<223> OTHER INFORMATION: Description of Artificial Sequence: VV40
      promoter sequence

<400> SEQUENCE: 8
ttgacgctcc cccaaaagcc cccttataat cgctgtggaa tagcttccaa aggaggtacg          60
gtatg                                                                     65

<210> SEQ ID NO 9
<211> LENGTH: 63
<212> TYPE: DNA
<213> ORGANISM: Artificial Sequence
<220> FEATURE:
<223> OTHER INFORMATION: Description of Artificial Sequence: VV37
      promoter sequence

<400> SEQUENCE: 9
ttgtagaggc ggcgctccgc ctctatggcc acccggatca tttaccccct catcaaggcc         60
acc                                                                       63

<210> SEQ ID NO 10

```
<211> LENGTH: 54
<212> TYPE: DNA
<213> ORGANISM: Artificial Sequence
<220> FEATURE:
<223> OTHER INFORMATION: Description of Artificial Sequence: VV53
      promoter sequence

<400> SEQUENCE: 10
ttgacaaagg ccatgcctcc ttggtatctt cccttttgcg ctgccctgag gggg            54

<210> SEQ ID NO 11
<211> LENGTH: 50
<212> TYPE: DNA
<213> ORGANISM: Artificial Sequence
<220> FEATURE:
<223> OTHER INFORMATION: Description of Artificial Sequence: VV18
      promoter sequence

<400> SEQUENCE: 11
ttgacaaggt cttccgccag gcctccatcc accacgtcat cgtcctggag                 50

<210> SEQ ID NO 12
<211> LENGTH: 50
<212> TYPE: DNA
<213> ORGANISM: Artificial Sequence
<220> FEATURE:
<223> OTHER INFORMATION: Description of Artificial Sequence: VV51
      promoter sequence

<400> SEQUENCE: 12
ttcgaatccc tccgggcccg ccattgttat cttggaaatg ggtagccttt                 50

<210> SEQ ID NO 13
<211> LENGTH: 51
<212> TYPE: DNA
<213> ORGANISM: Artificial Sequence
<220> FEATURE:
<223> OTHER INFORMATION: Description of Artificial Sequence: Terminator
      sequence

<400> SEQUENCE: 13
tgccacccca tgctggcttg cgccagcatg ggggccccgg caaaagaatt c               51

<210> SEQ ID NO 14
<211> LENGTH: 100
<212> TYPE: DNA
<213> ORGANISM: Artificial Sequence
<220> FEATURE:
<223> OTHER INFORMATION: Description of Artificial Sequence: PCR primer
      TR5KAN

<400> SEQUENCE: 14
acacacacac accatggcct aatgccaccc catgctggct tgcgccagca tgggggcccc      60
ggcaaaagaa ttcaaaggga atgagaatag tgaatggacc                           100

<210> SEQ ID NO 15
<211> LENGTH: 50
<212> TYPE: DNA
<213> ORGANISM: Artificial Sequence
<220> FEATURE:
<223> OTHER INFORMATION: Description of Artificial Sequence: PCR primer
      KAN3

<400> SEQUENCE: 15
gagcatggcc ctgcagaagc ttcaaaatgg tatgcgtttt gacacatcca                 50
```

<210> SEQ ID NO 16
<211> LENGTH: 39
<212> TYPE: DNA
<213> ORGANISM: Artificial Sequence
<220> FEATURE:
<223> OTHER INFORMATION: Description of Artificial Sequence: PCR primer
      3KM-RI

<400> SEQUENCE: 16
acacacgaat tccaaaatgg tatgcgtttt gacacatcc                              39

<210> SEQ ID NO 17
<211> LENGTH: 50
<212> TYPE: DNA
<213> ORGANISM: Artificial Sequence
<220> FEATURE:
<223> OTHER INFORMATION: Description of Artificial Sequence: PCR primer
      5KM-H3

<400> SEQUENCE: 17
cacacacaaa gctttacgta tctagaggga atgagaatag tgaatggacc                  50

<210> SEQ ID NO 18
<211> LENGTH: 97
<212> TYPE: DNA
<213> ORGANISM: Artificial Sequence
<220> FEATURE:
<223> OTHER INFORMATION: Description of Artificial Sequence: PCR primer
      VV3 7KM

<400> SEQUENCE: 18
acacacaagc ttgtagaggc ggcgctccgc ctctatggcc acccggatca tttacccct        60 catcaaggag gagaatagtg aatggaccaa taatgac                                97

<210> SEQ ID NO 19
<211> LENGTH: 96
<212> TYPE: DNA
<213> ORGANISM: Artificial Sequence
<220> FEATURE:
<223> OTHER INFORMATION: Description of Artificial Sequence: PCR primer
      VV53 KM

<400> SEQUENCE: 19
acacacacaa gcttgacaaa ggccatgcct ccttggtatc ttccttttg cgctgccctg        60 aggaggagaa tagtgaatgg accaataata atgact                                 96

<210> SEQ ID NO 20
<211> LENGTH: 96
<212> TYPE: DNA
<213> ORGANISM: Artificial Sequence
<220> FEATURE:
<223> OTHER INFORMATION: Description of Artificial Sequence: PCR primer
      VV18 KM

<400> SEQUENCE: 20
acacacacaa gcttgacaag gtcttccgcc aggcctccat ccaccacgtc atcgtcctgg       60
aggaggagaa tagtgaatgg accaataata atgact                                 96

<210> SEQ ID NO 21
<211> LENGTH: 96
<212> TYPE: DNA
<213> ORGANISM: Artificial Sequence
<220> FEATURE:
<223> OTHER INFORMATION: Description of Artificial Sequence: PCR primer
      VV51 KM

```
<400> SEQUENCE: 21
acacacaagc ttcgaatccc tccgggcccg ccattgttat cttggaaatg ggtagccttt        60
aggaggagaa tagtgaatgg accaataata atgact                                  96

<210> SEQ ID NO 22
<211> LENGTH: 100
<212> TYPE: DNA
<213> ORGANISM: Artificial Sequence
<220> FEATURE:
<223> OTHER INFORMATION: Description of Artificial Sequence: PCR primer
      VV57 KM

<400> SEQUENCE: 22
acacacacaa gcttgacaag ggaaagccgg ggtgctaact tagggattgc gctgccctca        60
tacgtaggag gagaatagtg aatggaccaa taataatgac                              100

<210> SEQ ID NO 23
<211> LENGTH: 89
<212> TYPE: DNA
<213> ORGANISM: Artificial Sequence
<220> FEATURE:
<223> OTHER INFORMATION: Description of Artificial Sequence: PCR primer
      VV12D2

<400> SEQUENCE: 23
acacacacaa gcttgacatt cccccgccc cgccgtaccc tccttcccgg gaggaggaga         60
atagtgaatg gaccaataat aatgactag                                          89

<210> SEQ ID NO 24
<211> LENGTH: 60
<212> TYPE: DNA
<213> ORGANISM: Artificial Sequence
<220> FEATURE:
<223> OTHER INFORMATION: Description of Artificial Sequence: VV1-2
      promoter sequence

<400> SEQUENCE: 24
ttgacattcc ccccgcccg gggtaccctc cttcccggga ggcgcgcctc ccgaggagaa         60

<210> SEQ ID NO 25
<211> LENGTH: 49
<212> TYPE: DNA
<213> ORGANISM: Artificial Sequence
<220> FEATURE:
<223> OTHER INFORMATION: Description of Artificial Sequence: VV1-2/D2
      promoter sequence

<400> SEQUENCE: 25
ttgacattcc ccccgccccg gggtaccctc cttcccggga ggaggagaa                    49

<210> SEQ ID NO 26
<211> LENGTH: 50
<212> TYPE: DNA
<213> ORGANISM: Artificial Sequence
<220> FEATURE:
<223> OTHER INFORMATION: Description of Artificial Sequence: Putative
      promoter sequence

<400> SEQUENCE: 26
atggcattgt ctttccgcta ttgaatgact atcattcaag tatggaaaga                   50

<210> SEQ ID NO 27
<211> LENGTH: 50
<212> TYPE: DNA
```

```
<213> ORGANISM: Artificial Sequence
<220> FEATURE:
<223> OTHER INFORMATION: Description of Artificial Sequence: Putative
      promoter sequence

<400> SEQUENCE: 27
gaggttgctt ggttccggtg cacgagttct attctgccca ggccgtagcg          50

<210> SEQ ID NO 28
<211> LENGTH: 50
<212> TYPE: DNA
<213> ORGANISM: Artificial Sequence
<220> FEATURE:
<223> OTHER INFORMATION: Description of Artificial Sequence: Putative
      promoter sequence

<400> SEQUENCE: 28
gagtacgttg accagcgctc cccgaaaggt ataagcgggc acgtaaagcc          50

<210> SEQ ID NO 29
<211> LENGTH: 50
<212> TYPE: DNA
<213> ORGANISM: Artificial Sequence
<220> FEATURE:
<223> OTHER INFORMATION: Description of Artificial Sequence: Putative
      promoter sequence

<400> SEQUENCE: 29
accttgtcgt gcctcgcctt gaggtagagg aacatggcgt agggctcctg          50

<210> SEQ ID NO 30
<211> LENGTH: 50
<212> TYPE: DNA
<213> ORGANISM: Artificial Sequence
<220> FEATURE:
<223> OTHER INFORMATION: Description of Artificial Sequence: Putative
      promoter sequence

<400> SEQUENCE: 30
ctaatctgga agtaggccgg gttcttggcg atgatctccc acaccagcac          50

<210> SEQ ID NO 31
<211> LENGTH: 50
<212> TYPE: DNA
<213> ORGANISM: Artificial Sequence
<220> FEATURE:
<223> OTHER INFORMATION: Description of Artificial Sequence: Putative
      promoter sequence

<400> SEQUENCE: 31
gacttgcaga aacttttggt aacctgccat agcttctacc ctcctcgttc          50

<210> SEQ ID NO 32
<211> LENGTH: 50
<212> TYPE: DNA
<213> ORGANISM: Artificial Sequence
<220> FEATURE:
<223> OTHER INFORMATION: Description of Artificial Sequence: Putative
      promoter sequence

<400> SEQUENCE: 32
tttgttaaag gaagcgagct ttcctcgcac ataattcacc agattcaaat          50

<210> SEQ ID NO 33
<211> LENGTH: 50
<212> TYPE: DNA
<213> ORGANISM: Artificial Sequence
```

```
<220> FEATURE:
<223> OTHER INFORMATION: Description of Artificial Sequence: Putative
      promoter sequence

<400> SEQUENCE: 33
gctcgcttcc tttaacaaag gtgatccggt actaaaaaat ctgcaagagg            50

<210> SEQ ID NO 34
<211> LENGTH: 50
<212> TYPE: DNA
<213> ORGANISM: Artificial Sequence
<220> FEATURE:
<223> OTHER INFORMATION: Description of Artificial Sequence: Putative
      promoter sequence

<400> SEQUENCE: 34
aacacgcatc tgattggcag acctttttcc agaatattgt tgaagaccgt            50

<210> SEQ ID NO 35
<211> LENGTH: 50
<212> TYPE: DNA
<213> ORGANISM: Artificial Sequence
<220> FEATURE:
<223> OTHER INFORMATION: Description of Artificial Sequence: Putative
      promoter sequence

<400> SEQUENCE: 35
tatgaccgtg gatgaagtca gtacctggcc gcggtcttat gggcacctgg            50

<210> SEQ ID NO 36
<211> LENGTH: 50
<212> TYPE: DNA
<213> ORGANISM: Artificial Sequence
<220> FEATURE:
<223> OTHER INFORMATION: Description of Artificial Sequence: Putative
      promoter sequence

<400> SEQUENCE: 36
gcaatcagaa tgtcaagcaa aaattggagt cgctcaaaat ccccgactcc            50

<210> SEQ ID NO 37
<211> LENGTH: 50
<212> TYPE: DNA
<213> ORGANISM: Artificial Sequence
<220> FEATURE:
<223> OTHER INFORMATION: Description of Artificial Sequence: Putative
      promoter sequence

<400> SEQUENCE: 37
caggtctagt ttggcgacgc gaggctcaag ggaataccgt cccggaccgc            50

<210> SEQ ID NO 38
<211> LENGTH: 50
<212> TYPE: DNA
<213> ORGANISM: Artificial Sequence
<220> FEATURE:
<223> OTHER INFORMATION: Description of Artificial Sequence: Putative
      promoter sequence

<400> SEQUENCE: 38
ttggttggtg tcttcggcca gaaaagggaa ataatcccag gtcatgcgcc            50

<210> SEQ ID NO 39
<211> LENGTH: 50
<212> TYPE: DNA
<213> ORGANISM: Artificial Sequence
<220> FEATURE:
```

```
<223> OTHER INFORMATION: Description of Artificial Sequence: Putative
      promoter sequence

<400> SEQUENCE: 39
aactggtttg aggcggcgct tcatctcgtc aaagtccacc aatcccggct              50

<210> SEQ ID NO 40
<211> LENGTH: 50
<212> TYPE: DNA
<213> ORGANISM: Artificial Sequence
<220> FEATURE:
<223> OTHER INFORMATION: Description of Artificial Sequence: Putative
      promoter sequence

<400> SEQUENCE: 40
gaagttttgt agcgagaccc aagagaaatc atgatatgag tgtggtactt              50

<210> SEQ ID NO 41
<211> LENGTH: 50
<212> TYPE: DNA
<213> ORGANISM: Artificial Sequence
<220> FEATURE:
<223> OTHER INFORMATION: Description of Artificial Sequence: Putative
      promoter sequence

<400> SEQUENCE: 41
gggaggccat cttgtctgga ttgtagcact tccctatcct tagcccaagg              50

<210> SEQ ID NO 42
<211> LENGTH: 50
<212> TYPE: DNA
<213> ORGANISM: Artificial Sequence
<220> FEATURE:
<223> OTHER INFORMATION: Description of Artificial Sequence: Putative
      promoter sequence

<400> SEQUENCE: 42
gtgcgcctat tttgagttct gcttcgtgga ggaggaagat ggctaagccg              50

<210> SEQ ID NO 43
<211> LENGTH: 50
<212> TYPE: DNA
<213> ORGANISM: Artificial Sequence
<220> FEATURE:
<223> OTHER INFORMATION: Description of Artificial Sequence: Putative
      promoter sequence

<400> SEQUENCE: 43
accccggggg gttgacgcac acccccgat ctgctaactt ggccttaagt               50

<210> SEQ ID NO 44
<211> LENGTH: 50
<212> TYPE: DNA
<213> ORGANISM: Artificial Sequence
<220> FEATURE:
<223> OTHER INFORMATION: Description of Artificial Sequence: Putative
      promoter sequence

<400> SEQUENCE: 44
gaccaacagc cattggcgca aagtaccaca ctcatatcat gatttctctt              50

<210> SEQ ID NO 45
<211> LENGTH: 56
<212> TYPE: DNA
<213> ORGANISM: Artificial Sequence
<220> FEATURE:
<223> OTHER INFORMATION: Description of Artificial Sequence: VV57
``` promoter clone insert sequence used as query sequence in BLASTN
analysis

<400> SEQUENCE: 45
gagctcatcg cctacggcct tagggttctt ctctcccttc tcccgccccc tccggg          56

<210> SEQ ID NO 46
<211> LENGTH: 56
<212> TYPE: DNA
<213> ORGANISM: Thermus thermophilus

<400> SEQUENCE: 46
gagctcatcg cctacggcct tagggttctt ctctcccttc tcccgccccc tccggg          56

<210> SEQ ID NO 47
<211> LENGTH: 73
<212> TYPE: DNA
<213> ORGANISM: Thermus thermophilus

<400> SEQUENCE: 47
tccccaggaa ccttttgccg ggcccccat gctggcgcaa gccagcatgg ggtggtgtta       60
caggtgccgc aga                                                        73

<210> SEQ ID NO 48
<211> LENGTH: 65
<212> TYPE: DNA
<213> ORGANISM: Thermus thermophilus

<400> SEQUENCE: 48
cagggacctt tgccggggc ccccatgctg gcgcaagcca gcatggggtg gcatcaaagc      60
acccc                                                                 65

<210> SEQ ID NO 49
<211> LENGTH: 46
<212> TYPE: DNA
<213> ORGANISM: Thermus thermophilus

<400> SEQUENCE: 49
ccatgccggg ccccatgccg gcccaagccg gcatggggtg gcctta                    46

<210> SEQ ID NO 50
<211> LENGTH: 48
<212> TYPE: DNA
<213> ORGANISM: Thermus thermophilus

<400> SEQUENCE: 50
ccttctgccg ggcccccat gcgggcgcaa gccgatgggg tggcctca                   48

<210> SEQ ID NO 51
<211> LENGTH: 53
<212> TYPE: DNA
<213> ORGANISM: Thermus thermophilus

<400> SEQUENCE: 51
gggccttttg ccggggcccc catgctggcg caagccagca tggggtggca tta             53

<210> SEQ ID NO 52
<211> LENGTH: 61
<212> TYPE: DNA
<213> ORGANISM: Thermus thermophilus

<400> SEQUENCE: 52

```
ttccccagaa aacctttgcc ggggccccca tgctggcttg ggccagcatg gggtggtatc    60
a                                                                    61
```